United States Patent [19]
Matsuki et al.

[11] Patent Number: 5,532,412
[45] Date of Patent: Jul. 2, 1996

[54] ULTRAVIOLET RAY-ABSORBING AROMATIC COMPOUND AND POLYMERIC COMPOSITION CONTAINING THE SAME

[75] Inventors: Toshitsugu Matsuki; Toshihiro Santa, both of Matsuyama, Japan

[73] Assignee: Teijin Limited, Osaka, Japan

[21] Appl. No.: 304,866

[22] Filed: Sep. 13, 1994

[30] Foreign Application Priority Data

Sep. 14, 1993 [JP] Japan .................. 5-228865

[51] Int. Cl.[6] .................. C07C 233/65
[52] U.S. Cl. ............ 564/158; 564/154; 564/155; 564/156; 524/223
[58] Field of Search .................. 564/158, 154, 564/155, 156; 524/223

[56] References Cited

FOREIGN PATENT DOCUMENTS

| 0071177 | 2/1982 | European Pat. Off. . |
| 552499 | 7/1993 | European Pat. Off. . |
| 0242390 | 4/1969 | U.S.S.R. . |

OTHER PUBLICATIONS

Derwent Abstract, JP-A-5 009 293, Teigin Ltd., Jan. 19, 1993.

Chemical Abstracts, vol. 73, No. 14, p. 52, Abstract 67646R, A. Cernaiani, Oct. 5, 1970, "Dyes, Fluorescent Whitening Agents".

Chemical Abstracts, vol. 71, No. 18, p. 37, Abstract No. 82123v, P. M. Bogatyrev, Nov. 3, 1969, "Plastics: Manufacture & Processing".

Chemical Abstracts, vo. 72, No. 24, p. 83, Abstract No. 26705-19-1, T Kuroda et al., Jun. 15, 1970, "Dyes".

Kuroda et al, Kogyo Kogaku Zasshi, 72(6), 1331–6, 1969.

*Primary Examiner*—Shailendra Kumar
*Attorney, Agent, or Firm*—Burgess, Ryan and Wayne

[57] ABSTRACT

An aromatic o-hydroxyamide compound of the formula (I)

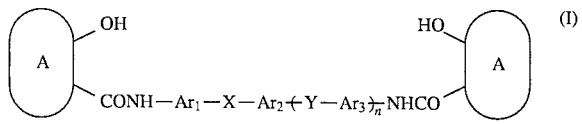

wherein the formula:

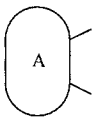

is a divalent aromatic group the formula:

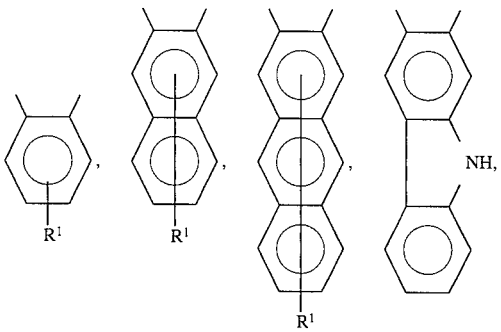

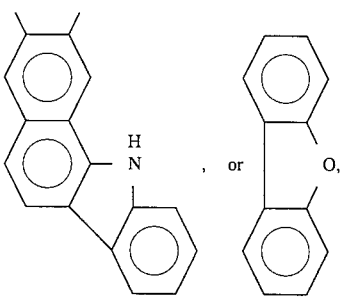

$R^1$=H, halogen, $C_{1-10}$ alkyl group, or $C_1$-alkoxyl group, $Ar_1$, $Ar_2$, $Ar_3$=a divalent aromatic groups, X, Y=O or S, and n=0 or 1, has an excellent ultraviolet ray-absorption and heat-resistance and is useful for enhancing an ultraviolet ray-resistance of polymeric materials, for example, wholly aromatic polyamide fibers.

1 Claim, 3 Drawing Sheets

Fig.1

ULTRAVIOLET RAY ABSORPTION OF NAD

Fig.2 C¹³−NMR SPECTRUM OF NAD

ULTRAVIOLET RAY-ABSORBING AROMATIC COMPOUND AND POLYMERIC COMPOSITION CONTAINING THE SAME

BACKGROUND OF THE INVENTION

1. Field of the Invention

The present invention relates to an aromatic o-hydroxyamide compound having an excellent ultraviolet ray absorption and heat resistance, and a polymeric composition containing the same and having an excellent ultraviolet ray resistance and mechanical strength.

2. Description of Related Art

It is known that conventional ultraviolet ray-absorbing benzophenone and benzotriazole compounds usually exhibit an ultraviolet ray-absorbing activity inherent to specific wavelengths of ultraviolet rays at a relatively low temperature. These conventional ultraviolet ray-absorbing compounds; however, exhibit an unsatisfactory thermal resistance, and thus are disadvantageous in that when the compounds are mixed into a polymeric material at a high temperature or the resultant mixture is shaped at a high temperature, most all of the compounds are thermally decomposed or sublimated.

As a measure to counter the above-mentioned disadvantage, it has been attempted to add an inorganic material, for example, fine particulate titanium dioxide, carbon black or red oxide to the polymeric material. However, this attempt is disadvantageous in that since the inorganic materials and the polymeric material are insoluble in each other, the addition of the inorganic materials usually causes the mixed polymeric material to have a reduced mechanical performance and to be colored, and thus the mixed polymeric material cannot keep a color inherent to the polymeric material per se.

Usually, polyesters, including wholly aromatic polyesters, aliphatic polyamides, wholly aromatic polyamides (aramids) and polycarbonates are mixed with an ultraviolet ray absorber during polymerization procedures, before or after shaping or molding procedures, or during post processing procedures thereof, at a high temperature to enhance their weathering resistance.

Since the conventional ultraviolet ray absorbers are unsatisfactory in thermal resistance, as mentioned above, a new type of organic ultraviolet ray absorbers having an enhanced ultraviolet ray-absorbing activity, thermal resistance and weathering resistance is in demand.

Especially, aramids have a high tensile strength, modulus and thermal resistance and thus are widely employed to produce fibers and films. However, it is well-known that aramids exhibit an unsatisfactory light resistance.

To enhance the light resistance of aramids, it has been attempted to mix an ultraviolet ray-absorbing benzotriazole compound and an anti-oxidant to a dope solution of poly-methaphenylene isophthalamide in N-methyl- 2-pyrrolidone, as disclosed in Japanese Unexamined Patent Publication (Kokai) No. 49-100,322. However, the light resistance of the resultant mixed polyamide is not always satisfactory.

Also, it is known that poly-para-phenylene terephthalamide (PPTA), which is a typical para-type aramid, is difficult to melt and to dissolve in common solvents. Therefore, to produce a shaped article, it is necessary to dissolve the p-aramid in a special solvent such as sulfuric acid and then the solution is subjected to a shaping process.

Although the usual meltable or soluble polymers can be mixed with various types of additives, which impact a specific performance to the polymers without difficulty, in the case of p-aramid, the additives capable of being mixed into the p-aramid solution in the sulfuric acid solvent are strictly restricted in view of the chemical stability of the additives to sulfuric acid. As an additive usable for the p-aramid solution, carbon black is known from Japanese Unexamined Patent Publication (Kokai) No. 64-85,316 and organic solvents are known from Japanese Unexamined Patent Publication (Kokai) No. 64-14,317.

However, the use of these materials causes the resultant aramid article to be colored in a specific color, and thus cannot be used to produce an aramid article having a color inherent to the aramid per se. Also, since the additives are difficult to evenly disperse in the p-aramid solution, the resultant p-aramid article exhibits an unsatisfactory mechanical strength.

Generally, where a conventional ultraviolet ray absorber is dissolved in an aramid dope solution, and the resultant dope solution is shaped, for example, into filaments, if the shaping temperature is high, the conventional ultraviolet ray absorber is usually decomposed and thus the resultant shaped article does not exhibit satisfactory light resistance.

Also, after shaping, in the resultant PPTA article, it is very difficult to fix an additive within the PPTA polymer due to a barrier derived from a high crystallinity and intermolecular chain force of the PPTA polymer. To enhance the light resistance of the para type aramid, it has been attempted to make an ultraviolet ray absorber to be contained in water-swollen, non-dried aramid fibers, as disclosed in Japanese Unexamined Patent Publication Nos. 49-75,824, 50-12,322, 53-35,020, 56-33,487 and 1-240,533. This attempt is, however, disadvantageous in that the impregnation of the p-aramid fiber with the ultraviolet ray absorber causes the intermolecular structure of the fiber to be disarranged and thus the mechanical properties such as tensile strength of the fiber are adversely affected.

Japanese Unexamined Patent Publication No. 5-9,293 discloses a method of enhancing the light resistance of the aramid by blending an aromatic amide compound having a naphthalene ring structure thereto. Where the compound is an oligomer produced by a polymerization different from that of the aramid, and the oligomer production is carried out at an industrial scale, generally, it is necessary to provide an oligomer producing reaction vessel separate from the aramid polymerization vessel and thus the number of the necessary reaction processes increases. If the aromatic amide compound has a lower molecular weight than that of the oligomer, the lower molecular weight amide compound sometimes sublimates during a heat-drawing or heat treating procedure. Also, most all of the fibers blended with the aromatic amide compound exhibit degraded mechanical properties.

Other attempts have been made to produce shaped articles from a blend of an aramide with an aromatic amide compound having a naphthalene ring stricture. For example, Japanese Unexamined Patent Publication No. 62-263,320 discloses a fiber consisting of a mixture of an aromatic copolyamide made by using a monomer having a naphthalene ring structure with a poly-paraphenylene terephthalamide, and Japanese Unexamined Patent Publication No. 3-143,922, especially Example 8 thereof, discloses an aramid fiber produced from a blend of a dope of an aramid having a naphthalene structure with a dope of another aramid having no naphthalene structure. The purpose of these attempts is to enhance the mechanical strength of the aramide fiber.

Japanese Examined Patent Publication (Kokoku) No. 62-10,580 discloses a method of improving the light resistance of a polyester, polycarbonate or polyamide by mixing a light heat resistant aromatic orthohydroxyamide compound, as an ultraviolet ray absorber, into the polymer. At the present time, it is well known that nylon polymers which are aliphatic polyamides are clearly distinguished from wholly aromatic polyamides, namely aramids. In the examples of the Japanese publication (Kokoku), only nylon 6 is employed as an example of the polyamide, and the Japanese publication is completely silent as to aramids. Also, although this Japanese publication discloses that aramids containing the aromatic orthohydroxyamide compound absorb ultraviolet rays at a specific wavelength or lower, the publication does not teach any mechanical property of the aramids. This is due to the fact that the aromatic orthohydroxyamide compound has a low solubility in the aramide and a poor heat resistance and exhibits an ultraviolet ray-shielding effect too low to prevent the deterioration of the aramide by the light. According, it is further demanded to provide a new ultraviolet ray absorber having an enhanced ultraviolet ray-shielding activity, heat resistance and compatibility with the aramids, and thus capable of enhancing the mechanical properties of the aramids. Further, among the aromatic hydroxyamide compounds disclosed in Japanese Examined Patent Publication No. 62-10,580, the compounds terminated at two ends thereof with naphthol carboxylic acid groups are provided with a middle diamine portion having a toxic benzidine structure, and thus this compound poses the risk of exhibiting toxicity when hydrolyzed.

Dokl Akad., Nauk BSSR, 23 (4), 347 (1979) and J. Appl. Polym. Sci., 23 (8), 2225 (1979) state that orthohydroxy salicylic acid amide compounds effectively enhance the light resistance of polymeric materials such as polyethylene or natural rubber. However, these compounds are unsatisfactory in ultraviolet ray-shielding activity and heat resistance. Also, these publications are completely silent as to the specific ultraviolet ray-absorbing compounds of the present invention and the specific advantages thereof.

SUMMARY OF THE INVENTION

An object of the present invention is to provide a new type of ultraviolet ray-absorbing aromatic compound having a high heat resistance and a polymeric composition containing the same.

Another object of the present invention is to provide a new type of ultraviolet ray-absorbing aromatic compound useful for producing a polymeric composition, especially an aramid composition, having a favorable mechanical properties, a high light resistance, and such a polymeric composition.

The above-mentioned objects can be attained by the ultraviolet ray-absorbing aromatic compound and the polymeric composition of the present invention.

The ultraviolet ray-absorbing aromatic compound of the present invention is an aromatic o-hydroxyamide compound of the formula (I);

wherein the formula;

represents a divalent aromatic group selected from those of the formulae:

R' represents a member selected from the group consisting of a hydrogen atom, halogen atoms, alkyl groups having 1 to 10 carbon atoms, and alkoxyl groups having 1 to 10 carbon atoms, $Ar_1$, $Ar_2$ and $Ar_3$ respectively and independently from each other represent a divalent aromatic group, X and Y respectively and independently from each other represent a member selected from the group consisting of oxygen and sulfur atoms, and n represents zero or one.

Also, the ultraviolet ray-absorbing agent of the present invention comprises, as an essential component, at least one aromatic o-hydroxyamide compound of the formula (I).

Further, the ultraviolet ray-resistant polymeric composition of the present invention comprises a matrix component consisting of a polymeric material and an ultraviolet ray-absorbing component consisting of at least one aromatic o-hydroxyamide compound of the formula (I), and in an amount of 0.01 to 10% by weight, bared on the weight of the matrix component.

DESCRIPTION OF THE PREFERRED EMBODIMENTS

The ultraviolet ray absorbing aromatic o-hydroxyamide compound of the present invention is a compound of the formula (I):

In the formula (I), the terminal groups of the formula:

are selected from the groups of the formulae:

preferably the groups of the formulae:

more preferably the groups of the formula:

In the above-mentioned formulae for the terminal groups, $R^1$ represents a member selected from the group consisting of a hydrogen atom, halogen atoms, for example, fluorine, chlorine, bromine and iodine atoms, alkyl groups having 1 to 10 carbon atoms, and alkoxyl groups having 1 to 10 carbon atoms,

Also, in the formula (I), $Ar_1$, $Ar_2$ and $Ar_3$, which may be the same as each other or different from each other, represent a divalent aromatic group preferably selected from the group consisting of p-phenylene m-phenylene, o-phenylene, 2,7-naphthalene, 2,6-naphthalene, 2,5-naphthalene, 2,4-naphthalene, 2,3-naphthalene, 1,2-naphthalene, 1,3-naphthalene, 1,4-naphthalene, 1,5-naphthalene, 1,6-naphthalene, 1,7-naphthalene, 1,8-naphthalene, 4,4'-biphenyl and 3,3'-biphenyl groups and groups of the formulae:

, and more preferably p-phenylene, m-phenylene, o-phenylene groups, still more preferably p-phenylene group.

The divalent aromatic groups represented by $Ar_1$, $Ar_2$ and $Ar_3$ in the formula (I) are optionally substituted with at least one substituent selected from the group consisting of alkyl groups having 1 to 10 carbon atoms, for example, methyl, ethyl, n-propyl, isopropyl, n-butyl, sec-butyl and test-butyl groups alkoxyl groups having 1 to 10 carbon atoms, for example, methoxyl, ethoxyl, isopropoxy and t-butoxy groups, and halogen atoms, for example, chlorine and bromine atoms.

Further, in the formula (I), X and Y, which may be the same as or different from each other, represent a member selected from the group consisting of oxygen and sulfur atoms and n represents zero or one.

The aromatic o-hydroxyamide compound of the formula is usable as an essential component of an ultraviolet ray-absorbing agent. The ultraviolet ray-absolving compound of the formula (I) is useful for protecting a polymeric material from deterioration due to ultraviolet rays.

The reasons for the protecting effect of the compound of the formula (I) for the polymeric material are assumed to be as follows.

When it is irradiated with light, the polymeric material is deteriorated by a specific wavelength band of light.

First, the specific wavelength band of light is absorbed by the terminal aromatic cyclic groups of the formula:

and the aromatic oxy or thio-amide groups which are highly sensitive to light.

Second, after the light absorption the aromatic compound is significantly stabilized by self-enol structures derived from the ortholydroxyl aromatic groups thereof.

The aromatic o-hydroxyamide compound of the present invention is preferably selected from those of the formulae:

and and is more preferably the compound of the formula:

The aromatic o-hydroxyamide compound of the formula (I) can be prepared by known synthesis methods. In one example of the synthesis methods, an aromatic o-hydroxycarboxylic acid of the formula:

is reacted with a hydroxyl group-blocking agent, for example, acetic arthydride or acetyl chloride to convent the hydroxyl group to a non-reactive group, and then the carboxyl group of the hydroxyl group-blocked compound is converted to an acid chloride group by a known method, and then the acid chloride group of the resultant compound is reacted with an aromatic diamine compound of the formula:

and then the blocked hydroxyl group is returned back to a hydroxyl group.

In another example of the synthesis methods, the above-mentioned hydroxyl group-blocked compound is directly reacted with the diamine compound under a high presume or in the presence of a catalyst, and then the blocked hydroxyl group is returned back to a hydroxyl group.

In still another example of the synthesis methods, the aromatic o-hydroxycarboxylic acid is esterified with a lower alcohol and then reacted with a diamine compound as mentioned above.

The synthesis method of the aromatic o-hydroxyamide compound of the present invention is, of course, not limited to the above-mentioned methods.

The ultraviolet ray-resistant polymeric composition of the present invention comprises a matrix component consisting of a polymeric material and an ultraviolet ray-absorbing component consisting of at least one aromatic o-hydroxyamide compound of the formula (I).

In the polymeric composition of the present invention, the ultraviolet ray-absorbing component is present in an amount of 0.01% to 10% by weight, preferably 0.1% to 8% by weight, based on the weight of the matrix component.

The content of the ultraviolet ray-absorbing component is set forth in consideration of the chemical structure and molecular weight of the ultraviolet ray-absorbing compound, and the type and composition of the polymeric material.

If the convent of the ultraviolet ray-absorbing component is less than 0.01% by weight, the resultant polymeric composition is sometimes unsatisfactory in ultraviolet ray-resistance.

The upper limit of the content of the ultraviolet ray-absorbing component is set forth in consideration of the compatibility of the ultraviolet ray-absorbing compound with the polymeric material and the desired mechanical property of the polymeric composition. Usually, the mechanical property of the polymeric composition is affected by an increase in the content of a low molecular weight additive, for example, the ultraviolet ray-absorbing compound.

The ultraviolet ray-absorbing compound of the present invention has a satisfactory compatibility with various types of polymeric materials, for example, synthetic resins and synthetic rubbers, and thus is suitable to produce a polymeric composition having a high stability and uniformity.

In the polymeric composition of the present invention, the matrix component comprises at least one polymeric material selected from, for example, polyvinyl chloride, polyvinylidene chloride, polyethylene, polypropylene, polymethyl methacrylate, polyacrylonitrile, polyesters including wholly aromatic polyesters, aliphatic polyamides, wholly aromatic polyamides (aramids), polycarbonates, polyurethanes, unsaturated polyesters, alkyd resins, thermosetting acrylic resins, epoxy resins, urea-aldehyde resins, melamine-aldehyde resins, phenolic compound-aldehyde resins, SBR and NBR, more preferably, the polyesters including wholly aromatic polyesters, aliphatic polyamides, wholly aromatic polyamides (aramids) and polycarbonates, still more preferably wholly aromatic polyamides (aramids).

The aramid usable for the present invention is produced by reacting at least one aromatic diamine with at least one aromatic dicarboxylic acid halide, and may be of a para-type or meta type. Preferably, the para-type aramide is used for the ultraviolet ray-resistant polymeric composition of the present invention.

In the preparation of the aramid, the aromatic diamine is preferably selected from the group consisting of p-phenylenediamine, m-phenylenediamine, benzidine, 4,4'-diamino-p-terphenyl, 2,7-diaminofluorene, 2,8-diaminophenoxathine, 1,4-, 1,5- and 2,6-naphthalenediamines, 3,3'-, 3,4'- and 4,4'-diaminodiphenylethers, 3,3'-, 3,4'-, and 4,4'- diaminodiphenylamides, 3,3'-, 3,4'- and 4,4'-diaminodiphenylsulfides, 3,3'-, 3,4'- and 4,4'-diaminodiphenylsulfones, 3,3'- 3,4'- and 4,4'-diaminobenzophenones, and 3,3-, 3,4' and 4,4'-diaminodiphenylmethanes, and derivatives of the above-mentioned compounds having at least one non-reactive substituent selected from lower alkyl groups preferably having 1 to 10 carbon atoms, lower alkoxyl groups preferably having 1 to 10 carbon atoms, halogen atoms and a nitro group, and attached to an aromatic ring structure thereof; and 2,2-bis-4-(4-aminophenoxy) phenylpropane, 2,2-bis-4-(3-aminophenoxy) phenylpropane, 2,2-bis-4-(4-aminophenoxy) phenylhexafluoropropane, 2,2-bis-4-(3-aminophenoxy) phenylhexafluoropropane, bis-4-(4-aminophenoxy) phenylsulfone, bis-4-(3-aminophenoxy) phenylsulfone, 1,4-bis-(4-aminophenoxy) benzene, 1,4-bis-( 3-aminophenoxy) benzene, 1,3-bis-(4-aminophenoxy) benzene, 1,3-bis-(3-aminophenoxy) benzene, 4,4'-bis-(4-aminophenoxy) biphenyl, 4,4-bis-(3-aminophenoxy) biphenyl, p-xylenediamine, m-xylenediamine, p-aminobenzylamine, m-aminobenzylamine, 9,10-bis-(4-aminophenyl) anthracene, and 9,9-bis-(4-aminophenyl) fluorene.

In the preparation of the aramid, the aromatic dicarboxylic acid halide is preferably selected from aromatic dicarboxylic acid chlorides, for example, terephthalic acid chloride, isophthalic acid chloride, 2,6- and 2,5-naphthalene dicarboxylic acid chlorides, and 4,4'-diphenyldicarboxylic acid chloride, which compounds may be substituted with at least one non-reactive group selected from, for example, lower alkyl groups, lower alkoxyl groups, halogen atoms and a nitro group.

The aramid useable for the present invention preferably contains repeating aromatic amide units in a content of at least 80 molar %, more preferably at least 90 molar %.

If the content of the repeating aromatic amide units is less than 80 molar %, the resultant aramid sometimes has an unsatisfactory heat resistance.

The repeating aromatic amide units are represented by the formula (II):

—HN—Ar$_4$—NHCO—Ar$_5$—CO—     (II)

wherein Ar$_4$ and Ar$_5$ respectively and independently from each other represent a divalent aromatic group selected from those of the formulae:

The divalent aromatic groups Ar$_4$ and Ar$_5$ of the above-mentioned formulae may be substituted with at least one substituent selected from halogen atoms and lower alkyl groups preferably having 1 to 10 carbon atoms.

In the repeating aromatic amide units of the formula (II), preferably at least 80 molar % of the total divalent aromatic groups represented by Ar$_4$ and Ar$_5$ are of the formula (III), (IV), (V) or (VI):

and the content of the divalent aromatic groups of the formula (IV) or (V) is 10 to 40 molar % based on the total molar amount of the divalent aromatic groups Ar$_4$ and Ar$_5$.

The ultraviolet ray-resistant polymeric composition of the present invention can be shaped into a film or filament or fiber. This shaping process is usually carried out by using a dope solution of the polymeric composition.

When the matrix polymer is an aramid, the dope solution can be prepared by mixing an ultraviolet ray-absorbing component into a solution polymerization product of the aramid, or by dissolving the aramid in a solvent and mixing the ultraviolet ray-absorbing component into the matrix polymer solution. In the preparation of the dope solution, a dissolving additive consisting of an inorganic salt may be added in an amount necessary to enhance the solubility of the aramid in the solvent. The inorganic salt is preferably selected from lithium chloride and calcium chloride.

The medium for the solution polymerization or the solvent for dissolving the aramid comprises preferably at least one non-protonic organic polar solvent selected from, for example, N-methyl-2-pyrrolidone, N-ethyl- 2-pyrrolidone, N,N-dimethylformamide, N,N-dimethylacetamide, N,N-diethylacetamide, N,N-dimethylpropionamide, N,N-dimethylbutylamide, N,N-dimethylisobutylamide, N-methylcaprolactam, N,N-dimethylmethoxyacetamide, N-acetylpyrrolidine, N-acetylpiperidine, N-methylpiperidone-2, N,N'-dimethylethyleneurea, N,N'-dimethyl-propyleneurea, N,N.N',N'-tetramethylmalonamide, N-acetylpyrrolidone, N,N. N',N'-tetramethylurea and dimethylsulfoxide.

The aramid usable for the present invention is not limited to one having a specific degree of polymerization, generally, as for as the aramid can be dissolved in the solvent, the higher the degree of polymerization of the aramid, the better the resultant polymeric composition.

When the aramid is prepared by a solution polymerization, usually, the dicarboxylic acid component and the diamine component are reacted in a substantially equimolar amount to each other. To control the degree of polymerization, one of the dicarboxylic acid and diamine components may be employed in an excessive molar amount. Also, a terminal-blocking agent, for example, a monofunctional acid compound or amine compound may be added to the solution polymerization system.

The ultraviolet ray-absorbing component of the present invention can be incorporated into the matrix component by any method. For example, the ultraviolet ray-absorbing component is directly added to the matrix component immediately before the resultant polymeric composition is subjected to a shaping step or processing step. In another example, a resin compound (blend) is prepared from an ultraviolet ray-absorbing component and a matrix component and then processed. In still another example, a master batch is prepared from a matrix component mixed with a high content of an ultraviolet ray-absorbing component, and mixed with an additional amount of the matrix component, and then the mixture is processed. In a further example, a matrix component polymer is prepared from a polymerization system containing the ultraviolet ray-absorbing component. Any of the above-mentioned examples can be applied to the preparation of the ultraviolet ray-resistant polymeric composition of the present invention, without difficulty.

Particularly, the incorporation of the ultraviolet ray-absorbing compound of the present invention into an aramid can be carried out as follows.

Where an aramid dope solution is prepared from a solution polymerization product without isolating the aramid therefrom, preferably, the ultraviolet ray-absorbing component per se, or a slurry or solution thereof is added to the solution polymerization system after the neutralization step of the polymerization system but before the shaping step of the resultant dope solution. If the ultraviolet ray-absorbing component is added to the polymerization system before the polymerization thereof, the non-reacted aromatic dicarboxylic acid halide is reacted with the hydroxyl groups of the ultraviolet ray-absorbing compound of the present invention, and thus reaction sometimes binders the polymerization for the aramid.

Where the aramid dope solution is prepared by dissolving the aramid in a solvent, the ultraviolet ray-absorbing component per se or a slurry or solution thereof may be directly added to the dissolving system of the aramid. In another example, the ultraviolet ray-absorbing component is added into the dope solution immediately before the shaping or processing step. The addition can be effected by a dynamic procedure using agitating wings or an extruder or a static procedure using a static mixer.

In the polymeric composition, the matrix component and the ultraviolet ray-absolving component are preferably uniformly mixed and dissolved in each other, to provide a shaped article having satisfactory mechanical properties. However, the ultraviolet ray-absorbing component may be dispersed in the matrix component as far as the resultant shaped article exhibits satisfactory mechanical properties.

The polymeric composition can be shaped by any shaping method. Where the matrix component comprises an aramid, the aramid composition is converted to a dope solution and then shaped by a wet-shaping method. When shaped into filaments by a wet-spinning method, the aramide dope solution may be directly extruded into a coagulating bath. The coagulating bath is comprised of a bad solvent for the aramide. Usually, the bad solvent is mixed with a good solvent to control the coagulating rate to a level at which the solvent of the dope solution is extracted at an appropriate extracting rate by the coagulating liquid and no defects are formed in the resultant coagulated aramid filaments. Usually, the bad solvent consists of water, and the good solvent consists of the same solvent as that in the dope solution. The mixing ratio of the good solvent to the bad solvent is variable depending on the dissolving and coagulating properties of the aramide, and preferably is in the range of from 15/85 to 40/60.

The ultraviolet ray-absorbing agent or component for the polymeric composition of the present invention may consist of a single type of ultraviolet ray-absorbing compound or a mixture of two or more different types of ultraviolet ray-absorbing compounds.

Also, the ultraviolet ray-absorbing agent of the present invention can be employed together with an additional selected from conventional ultraviolet ray-absorbers, light stabilizes and anti-oxidants. Further, the ultraviolet ray-absorbing agent of the present invention may be used together with another addition, for example, a plasticizer, emulsifier, lubricant, pigment, fluorescent brightening agent, flame-retardant and/or antistatic agent.

The ultraviolet ray-resistant polymeric composition of the present invention can be shaped into any form, for example, a filament, pulp, powder, film, tape and sheet. The pulp or powder can be compression molded or spread-casted into a shaped article, for example, film or sheet.

The aromatic o-hydroxyamide compound of the formula (I) of the present invention exhibits a ultraviolet ray-absorbing activity comparative to conventional ultraviolet ray-absorbing agents and a heat resistance significantly higher than conventional ones. Also, the polymeric composition of the present invention exhibits an excellent ultraviolet ray-resistance, a high heat stability and a low sublimation property. Therefore, the aromatic o-hydroxyamide compound of the present invention can impart, even in a small amount, a high weathering resistance to the polymeric material, especially an aramid, without degrading the mechanical properties of the polymeric material.

EXAMPLES

The present invention will be further explained by way of the following specific examples which are merely representative and do not restrict the scope of the present invention in any way.

In the examples, the term "part" refers to—part by weight—.

Example 1

(1) Preparation of 2-naphthol-3-amide compound of the formula:

This compound will be referred to as "NAD" hereinafter 2-hydroxy-3-naphthoic acid was heated at a temperature of 70° C. in a large amount of acetic anhydride for one hour, the reaction mixture was concentrated in an evaporator and the concentrated product was spread in a large amount of water and left to stand at room temperature for one night. Then, the resultant precipitate was collected by filtration and recrystallized from a mixture of acetic acid and water in a mixing weight ratio of 2/1. The resultant crystals were collected from the recrystallization liquid, dried, and thereafter heat treated in a large amount of thionyl chloride at a temperature of 70° C. for one hour. When the reaction mixture was cooled, crystals were generated. The crystals were collected from the reaction mixture by filtration, and dried. The crystals in an amount of 74.6 g (0.3 mole) were reacted with 43.8 g (0.15 mole) of 1.4-bis-(4-aminophenoxy) benzene in 500 ml of N-methyl- 2-pyrrolidone at a temperature of 100° C. for 30 minutes. After the reaction was completed, the resultant reaction mixture was spread in a large amount of water. The resultant precipitate was collected by filtration. The precipitate was treated in 1500 ml of a mixture of a 10% aqueous potassium carbonate solution with methyl alcohol in a mixing weight ratio of 1/1, at a temperature of 60° C. for 2 hours. This treated mixture was mixed with a 1N aqueous hydrochloric acid solution to adjust the pH of the mixture to about 4. A precipitate was generated from the mixture. The precipitate was collected by filtration and recrystallized from N.N-dimethylsulfoxide. NAD was obtained in an amount of 59.7 g. The yield of NAD based on 1.4-bis-(4-aminophenoxy) benzene was 63%.

(2) Analysis

A portion of the resultant NAD was subjected to the following measurements.

(a) Ultraviolet ray absorption

A solution of NAD in dimethyl formamide (DMF) was prepared in a concentration of $2 \times 10^{-5}$ g/ml.

Figure 1:
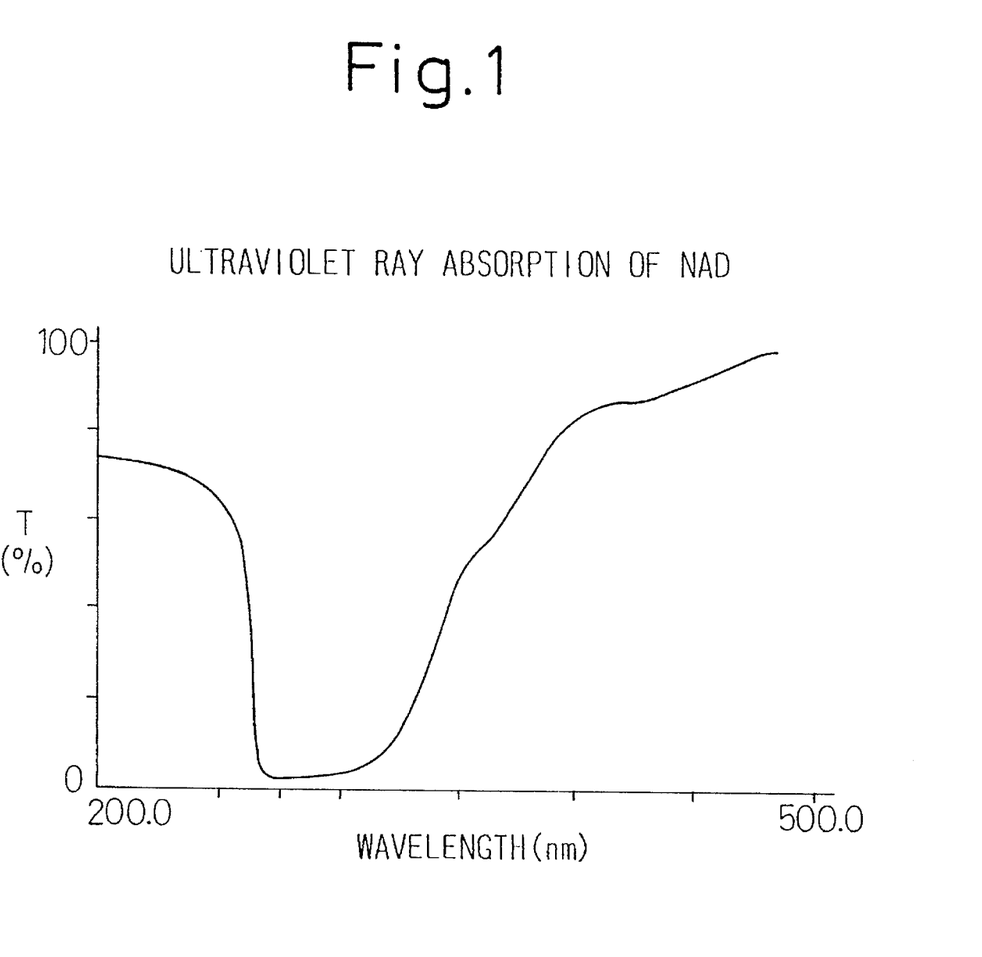
FIG. 1 is a chart showing the ultraviolet ray absorption spectrum of an aromatic o-hydroxyamide compound of the present invention.

The transmittance (T%) of ultraviolet rays in a wavelength band of from 200 nm to 500 nm through the NAD solution was measured. The result is shown in FIG. 1.

(b) Carbon$^{13}$ nuclear magnetic resonance ($C^{13}$-NMR) spectral analysis.

Figure 2:
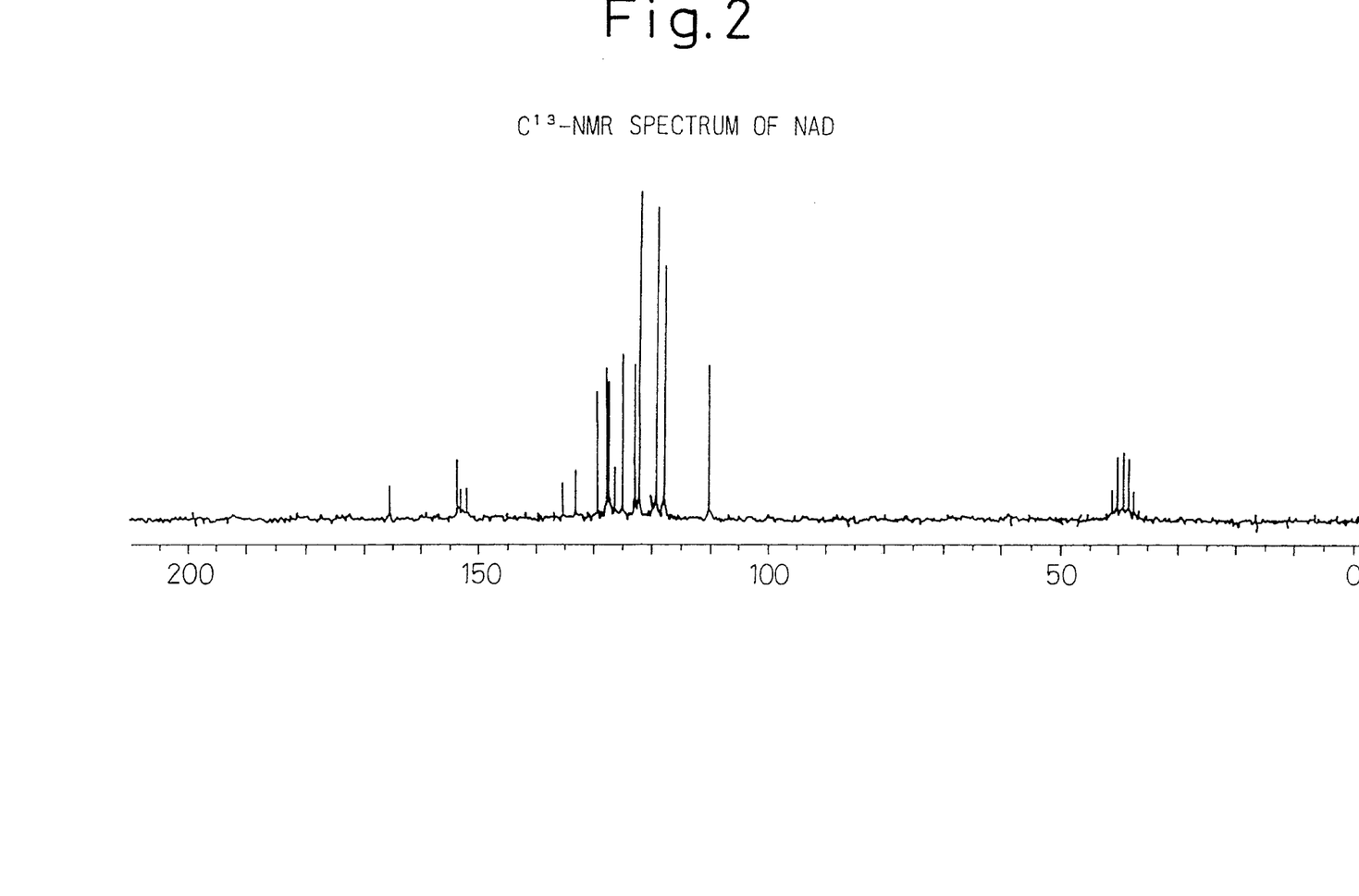
FIG. 2 is a chart showing the $C^{13}$-NMR spectrum of the aromatic o-hydroxyamide compound of the present invention.

The NAD crystals exhibited the $C^{13}$-NMR spectrum shown in FIG. 2.

(c) Infrared spectroscopic analysis

Figure 3:
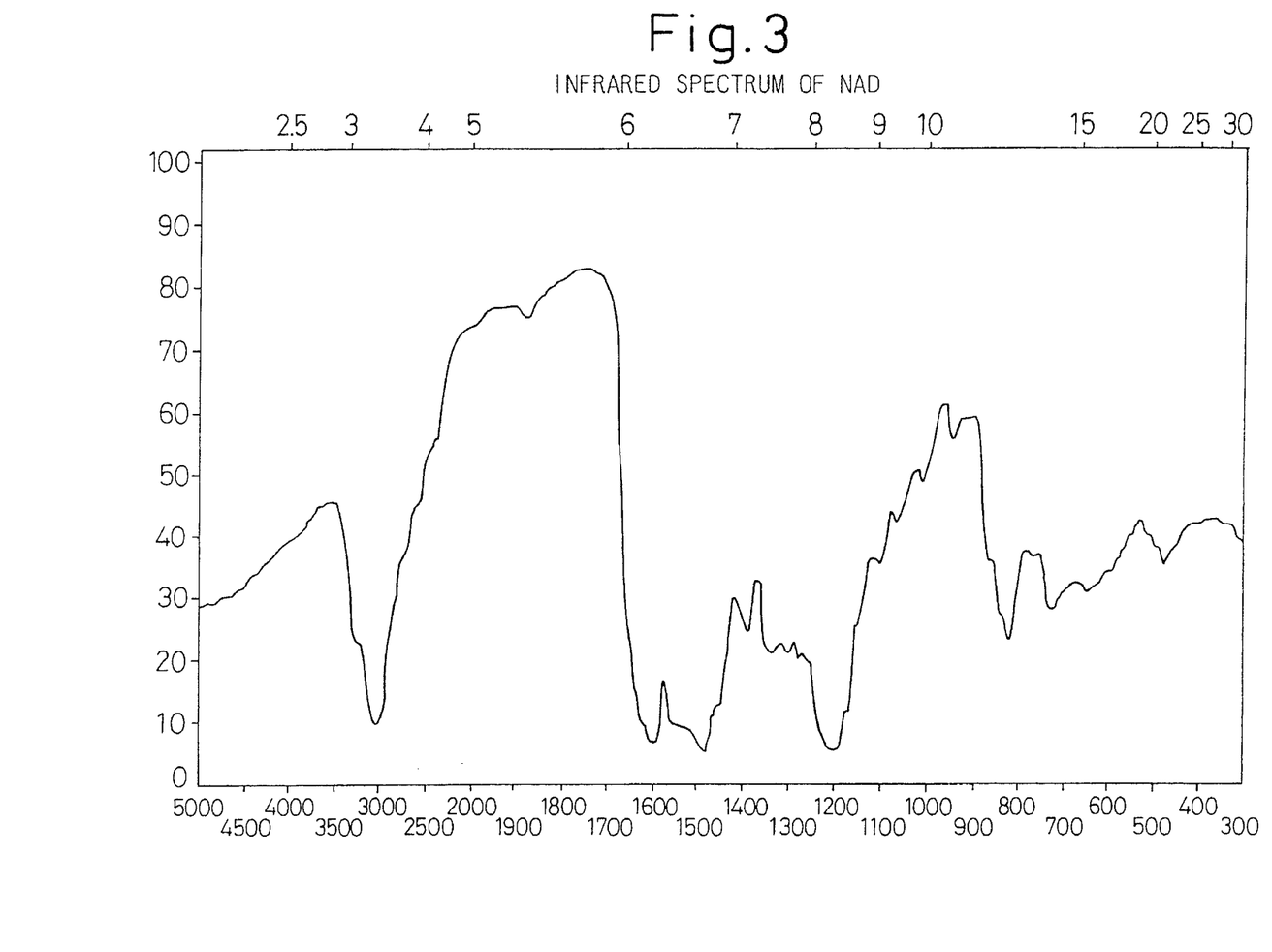
FIG. 3 is a chart showing the infrared spectrum of the aromatic o-hydroxyamide compound of the present invention.

The NAD crystals exhibited the infrared spectrum shown in FIG. 3.

(d) Thermal decomposition mass spectrometric analysis.

NAD had a molecular weight of 632.2 determined by a thermal decomposition mass spectrometric analysis. This was consistent with that calculated from the chemical formula of NAD. NAD had a melting point of 358° C. and a λmax of 302 nm.

(3) Preparation of aramid composition (a) Preparation of aramid dope solution.

A fully dried three-necked flask equipped with a stirrer was charged with 112.9 parts of N-methyl- 2-pyrrolidone which will be referred to as NMP hereafter, 1.506 parts of p-phenylenediamine and 2.789 parts of 3,4'-diaminodiphenylether at room temperature, and the amino compounds were dissolved in NMP while flowing nitrogen gas through the inside of the flask. Then, 5.658 parts of terephthalic acid chloride were added into the solution in the flask while stirring the reaction mixture. The reaction mixture was heated at a temperature of 85° C. for 60 minutes. A clear and viscous polymer solution was obtained. A slurry of 2.5% by weight of calcium hydroxide in NMP was added in an amount of 9.174 parts into the polymer solution to neutralize it. The resultant polymer had a logarithmic viscosity of 3.41 determined in a constant temperature bath at a temperature of 100° C. by the falling ball method using a steel ball made from SUS316 having an outside diameter of 3 nm. The resultant dope solution had a concentration of polymer (aramid) of 6,000% by weight (7.921 parts).

(b) Addition of NAD into aramid dope solution

A 20% NAD solution in NMP was mixed in a NAD concentration of 3% by weight into the aramid dope solution, to prepare a spinning dope solution.

(4) Spinning

The spinning dope solution was extruded through a spinneret having 100 spinning orifices each having an inside diameter of 0.3 mm, and the extruded filamentary streams of the dope solution were introduced into and coagulated in a coagulating liquid consisting of an aqueous solution of 30% by weight of NMP. The distance between the outside ends of the spinneret and the level surface of the coagulating liquid was 8 mm. The coagulated filaments were withdrawn from the coagulating liquid, washed with water, dried, and drawn on heating plates in two steps, namely in a first step at 390° C. at a draw ratio of 2.5 and in a second step at 52° C. at a draw ratio which caused the total draw ratio to become equal to 80% of the ultimate (maximum) elongation of the coagulated filaments. The drawn filament yarn was wound around a winding roll. The filament yarn had a yarn count of 166.7 d tex (150 denier)/100 filaments.

The resultant aramide composition filaments had the tensile strength and ultimate elongation as shown in Table 1.

(5) Weathering test

A portion of the aramid composition filaments was subjected to a sunshine weathering test in accordance with Japanese Industrial Standard (JIS) L0842, at a temperature of 63° C. with periodical showering, for 100 hours.

After the test, the tensile strength and ultimate elongation of the tested filaments were measured and then retensions of the tensile strength and ultimate elongation were calculated. The results are shown in Table 1.

Comparative Example 1

The same procedures and tests as in Example 1 were carried out except that the addition of NAD to the aramid solution was omitted. The test results are shown in Table 1. From Table 1, it is understood that the omission of NAD results in a significantly reduced weathering resistance of the aramid filaments.

Comparative Example 2

The same procedures and tests as in Example 1 were carried out except that NAD was replaced by 3% by weight of Naphthol AS-BR which is a trademark of an ultraviolet ray absorber made of Hoechst, based on the weight of the aramid. The test results are shown in Table 1. The resultant aramid composition filaments had a weathering resistance higher than that of Comparative Example 1 in which no ultraviolet ray-absorber was used, but lower than that of Example 1 in which NAD was used.

Example 2

The same procedures and tests as in Example 1 were carried out except that NAD was added in an amount of 0.01% by weight. The test results are shown in Table 1.

Comparative Example 3

The same procedures as tests as in Example 1 were carried out except that NAD was employed in an amount of 0.005% by weight. The test results are shown in Table 1. The resultant aramid composition filaments exhibited unsatisfactory weathering resistance.

Example 3

The same procedures and tests as in Example 1 were carried out except that NAD was employed in an amount of 10% by weight. The test results are shown in Table 1.

Comparative Example 4

The same procedures and tests as in Example 1 were carried out except that NAD was employed in an amount of 15% by weight.

The test results are shown in Table 1. The resultant aramid composition filaments exhibited unsatisfactory mechanical properties.

Example 4

The same procedures and tests as in Example 1 were carried out except that NAD was melt-mixed in an amount of 1% by weight into polyethylene terephthalate at a temperature of 385° C. for 10 minutes, and the resultant polyester composition was melt-spun into filaments having a yarn count of 83.3 d tex (75 denier)/48 filaments.

The test results are shown in Table 1.

Comparative Example 5

The same procedures and tests in Example 4 were carried out except that the addition of NAD was omitted. The test results are shown in Table 1. The resultant polyester filaments exhibited a significantly lower weathering resistance than that of Example 4.

Example 5

The same procedures and tests as in Example 4 were carried out except that the polyester was replaced by nylon 6, the melt mixing of NAD into nylon 6 was carried out at a temperature of 260° C. for 10 minutes, and the nylon 6 composition melt was converted to filaments having a yarn count of 77.8 d tex (70 denier)/48 filaments.

The test results are shown in Table 1.

Comparative Example 6

The same procedures and tests as in Example 5 were carried out except that the addition of NAD was omitted.

The test results are shown in Table 1.

The resultant nylon 6 filaments exhibited a significantly lower weathering resistance than that of Example 5.

Example 6

The same procedures tests as in Example 1 were carried out except that in the preparation of the ultraviolet ray-absorbing compound, 1.4-bis-( 4-aminophenoxy) benzene was replaced by 1.4-bis-( 4-aminothiophenoxy) benzene, and thus NAD was replaced by the thionaphthol amide compound of the formula:

This compound will be referred to as NAPS hereinafter.

NAPS was dissolved in a concentration of 20% by weight in NMP and the NAPS solution was mixed into the aramid solution to provide an aramid composition dope solution containing 3% by weight of NAPS based on the weight of the aramid polymer.

The test results are shown in Table 1.

The weathering resistance of the resultant aramid composition filaments was satisfactory.

TABLE 1

| Item | UV-absober | Matrix polymer | Amount of UV absorber (wt %) | Total d tex of filaments | Before weathering test | | After weathering test | | | |
|---|---|---|---|---|---|---|---|---|---|---|
| | | | | | Tensile strength (g/d tex) | Ultimate elongation (%) | Tensile strength (Retention) | | ultimate elongation (Retention) | |
| | | | | | | | (g/d tex) | (%) | (%) | (%) |
| Example 1 | NAD | Aramid | 3 | 166.7 | 26.1 | 4.30 | 16.7 | (64%) | 3.28 | (77%) |
| Comparative Example 1 | — | Aramid | — | 166.7 | 25.2 | 4.10 | 11.9 | (47%) | 2.26 | (55%) |
| Comparative Example 2 | AS-BR | Aramid | 3 | 166.7 | 25.3 | 4.21 | 14.4 | (57%) | 2.82 | (67%) |
| Example 2 | MAD | Aramid | 0.01 | 167.8 | 25.5 | 4.15 | 13.2 | (52%) | 2.57 | (62%) |
| Comparative Example 3 | NAD | Aramid | 0.005 | 167.8 | 25.3 | 4.11 | 12.4 | (49%) | 4.24 | (59%) |
| Example 3 | NAD | Aramid | 10 | 166.7 | 23.9 | 3.92 | 16.5 | (69%) | 3.02 | (77%) |
| Comparative Example 4 | NAD | Aramid | 15 | 167.8 | 23.3 | 3.84 | 15.8 | (68%) | 2.92 | (76%) |
| Example 4 | NAD | Polyester | 1 | 83.3 | 3.9 | 24 | 2.4 | (63%) | 18.0 | (75%) |
| Comparative Example 5 | — | Polyester | — | 83.3 | 3.9 | 25 | 1.7 | (45%) | 12.5 | (50%) |
| Example 5 | NAD | Nylon | 1 | 77.8 | 4.6 | 41 | 3.2 | (68%) | 31.6 | (77%) |
| Comparative Example 6 | — | Nylon | — | 77.8 | 4.6 | 41 | 2.3 | (51%) | 24.2 | (59%) |
| Example 6 | NAPs | Aramid | 3 | 166.7 | 24.2 | 3.96 | 14.6 | (60%) | 3.01 | (76%) |

Example 7

NAD was melt-mixed in an amount of 1% by weight in a polycarbonate at a temperature of 280° C. and the polycarbonate composition melt was converted to a film having a thickness of 400 μm.

The film was placed 15 cm from an ultraviolet ray lamp (available under a trademark of Photochemical Lamp H-400P from Toshiba) and the film was irradiated with ultraviolet rays from the lamp for one hour. It was confirmed that the film was not discolored and the mechanical strength of the film was not reduced.

Comparative Example 7

The same procedures and tests as in Example 7 were carried out except that no NAD was added.

After the ultraviolet ray irradiation test, it was found that the film was discolored and easily broken on contact with the experimenter's fingers.

We claim:

1. An aromatic o-hydroxyamide compound of the formula (I):

wherein X and Y respectively and independently from each other represent a member selected from the group consisting of oxygen and sulfur atoms, and represents a divalent aromatic group selected from those of the formula:

, and

* * * * *